(12) United States Patent
Goebbel et al.

(10) Patent No.: US 7,408,074 B2
(45) Date of Patent: Aug. 5, 2008

(54) METHOD FOR PRODUCING AN ALKENE OXIDE

(75) Inventors: Hans-Georg Goebbel, Kallstadt (DE); Peter Bassler, Viernheim (DE); Joaquim Henrique Teles, Otterstadt (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 290 days.

(21) Appl. No.: 10/553,516

(22) PCT Filed: Apr. 16, 2004

(86) PCT No.: PCT/EP2004/004077

§ 371 (c)(1),
(2), (4) Date: Oct. 14, 2005

(87) PCT Pub. No.: WO2004/092149

PCT Pub. Date: Oct. 28, 2004

(65) Prior Publication Data

US 2006/0276662 A1    Dec. 7, 2006

(30) Foreign Application Priority Data

Apr. 16, 2003   (DE) ................ 103 17 520

(51) Int. Cl.
*C07D 301/12* (2006.01)
(52) U.S. Cl. .................. 549/531; 203/23
(58) Field of Classification Search .......... 549/531; 203/23, 86
See application file for complete search history.

(56) References Cited

FOREIGN PATENT DOCUMENTS

| | | |
|---|---|---|
| DE | 100 01 401 | 7/2001 |
| EP | 0 311 983 | 4/1989 |
| EP | 0 405 978 | 1/1991 |
| EP | 0 573 887 | 12/1993 |
| EP | 0 659 473 | 6/1995 |
| EP | 0 719 768 | 7/1996 |
| EP | 1 247 805 | 10/2002 |
| EP | 1 285 915 | 2/2003 |
| WO | 98/55228 | 12/1998 |
| WO | 98/55229 | 12/1998 |
| WO | 98/55430 | 12/1998 |
| WO | 00/07965 | 2/2000 |

OTHER PUBLICATIONS

Meier et al., Atlas of Zeolite Structure Types, 4th Ed. London (1996).
Xu et al., "Oxidative Dehydrogenation of Propane", React. Kinet. Catal. Lett, vol. 57, No. 1, pp. 3-11 (1996).
Delmon, "The Future of Industrial Oxidation Catalysis Spurred by Fundamental Advances", 3rd World Congress on Oxidation Catalysis, 110, pp. 43-59 (1997).

*Primary Examiner*—Janet L Andres
*Assistant Examiner*—David E Gallis
(74) *Attorney, Agent, or Firm*—Oblon, Spivak, McClelland, Maier & Neustadt, P.C.

(57) ABSTRACT

Process for preparing an alkene oxide, which comprises at least the steps (i), (ii) and (v):

(i) providing a stream S1 comprising compressed, liquid alkene;

(ii) depressurizing at least part of the stream S1 with absorption of heat and with at least partial vaporization of the liquid alkene;

(v) reacting the alkene obtained in (ii) with a hydroperoxide in the presence of at least one solvent and at least one catalyst to give a mixture comprising alkene oxide and the solvent or solvents.

16 Claims, No Drawings

METHOD FOR PRODUCING AN ALKENE OXIDE

The present invention relates to a process for preparing an alkene oxide, in which a stream of a compressed, liquid alkene is depressurized with vaporization of at least part of the alkene and, in a preferred embodiment of the invention, the heat absorbed as a result of the depressurization is used to provide refrigeration in at least one step of the process of the present invention and thus achieve heat integration in the total process.

In processes for preparing alkene oxides, for example processes for preparing propylene oxide from propene, an alkene stream which is procured on an industrial scale in liquid form under some pressure via pipes is frequently fed into the process for reaction. The liquid alkene is normally mixed, for example, into a solvent used for the reaction before being converted into the corresponding alkene oxide.

It is an object of the present invention to provide a process which utilizes at least part of the energy contained in the compressed alkene stream.

We have found that this object is achieved by a process for preparing an alkene oxide, which comprises at least the steps (i), (ii) and (v):

(i) providing a stream S1 comprising compressed, liquid alkene;
(ii) depressurizing at least part of the stream S1 with absorption of heat and with at least partial vaporization of the liquid alkene;
(v) reacting the alkene obtained in (ii) with a hydroperoxide in the presence of at least one solvent and at least one catalyst to give a mixture comprising alkene oxide and the solvent or solvents.

In the process of the present invention, the alkene used in (i) can be any alkene which can be compressed to give a liquid stream S1 and reacted with a hydroperoxide to give the corresponding alkene oxide. The term "alkene" as used in the context of the present invention refers to all compounds which have at least one C-C double bond. In particular, the process of the present invention can be carried out using, for example, the following alkenes:

ethene, propene, 1-butene, 2-butene, isobutene, butadiene, pentenes, piperylene, hexenes, hexadienes, methylenecyclopropane, cyclopentene, cyclohexene, vinyloxirane, vinylidene fluoride, allyl halides, crotyl chloride, methallyl chloride, dichlorobutene, allyl alcohol, methallyl alcohol, butenols, butenediols, cyclopentenediols, pentenols, ethoxyethene, unsaturated carboxylic acids such as acrylic acid, methacrylic acid, crotonic acid, maleic acid, vinylacetic acid and mixtures of two or more of these compounds.

In the process of the present invention, preference is given to using alkenes which have from 2 to 6 carbon atoms. Particular preference is given to using propene as alkene in the process of the present invention.

Accordingly, the present invention provides a process as described above in which the alkene present in the stream S1 is propene.

In the process of the present invention, at least one hydroperoxide is reacted with the alkene. For the purposes of the present invention, the term "hydroperoxide" refers to a compound of the formula ROOH. Details regarding the preparation of hydroperoxides and regarding hydroperoxides which can, inter alia, be used in the process of the present invention may be found in DE-A 198 35 907, whose relevant contents are incorporated by reference into the disclosure of the present patent application. Examples of hydroperoxides which can be used according to the present invention are, inter alia, tert-butyl hydroperoxide, ethylbenzene hydroperoxide, tert-amyl hydroperoxide, cumene hydroperoxide, cyclohexyl hydroperoxide, methylcyclohexyl hydroperoxide, tetrahydronaphthalene hydroperoxide, isobutylbenzene hydroperoxide, ethylnaphthalene hydroperoxide, peracids such as peracetic acid or hydrogen peroxide. Mixtures of two or more hydroperoxides can also be used according to the present invention. Preference is given to using hydrogen peroxide as hydroperoxide for the purposes of the present invention, and particular preference is given to using an aqueous hydrogen peroxide solution.

Accordingly, the present invention provides a process as described above in which the hydroperoxide used in (v) is hydrogen peroxide.

The catalysts which can be used in the process of the present invention are subject to no particular restrictions, as long as the alkene used can be converted into the corresponding alkene oxide in the presence of the catalysts. Particular preference is given to using zeolite catalysts in the process of the present invention.

Zeolites are, as is known, crystalline aluminosilicates having ordered channel and cage structures and having micropores which are preferably smaller than about 0.9 nm. The network of such zeolites is made up of $SiO_4$ and $AlO_4$ tetrahedra which are joined via shared oxygen bridges. An overview of the known structures may be found, for example, in W. M. Meier, D. H. Olson and Ch. Baerlocher, "Atlas of Zeolite Structure Types", Elsevier, 5th edition, Amsterdam 2001.

Zeolites which contain no aluminum and in which part of the Si(IV) in the silicate lattice has been replaced by titanium as Ti(IV) are also known. These titanium zeolites, in particular those having a crystal structure of the MFI type, and possible ways of preparing them are described, for example, in EP-A 0 311 983 or EP-A 0 405 978. Apart from silicon and titanium, such materials may further comprise additional elements such as aluminum, zirconium, tin, iron, cobalt, nickel, gallium, germanium, boron or small amounts of fluorine. In the zeolite catalysts which have preferably been regenerated using the process of the present invention, the titanium of the zeolite can have been partially or completely replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, particularly those having a crystal structure of the MFI type, and possible ways of preparing them are described, for example, in WO 98/55228, EP-A 0 311 983 or EP-A 0 405 978, whose relevant contents are fully incorporated by reference into the disclosure of the present patent application.

It is known that titanium zeolites having an MFI structure can be identified via a particular X-ray diffraction pattern and additionally via a lattice vibration band in the infrared region (IR) at about 960 $cm^{-1}$ and thus differ from alkali metal titanates or crystalline and amorphous $TiO_2$ phases.

Specific examples of zeolites which can be used are titanium-, germanium-, tellurium-, vanadium-, chromium-, niobium- and zirconium-zeolites having a pentasil zeolite structure, in particular the types which can be assigned X-ray-crystographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structures and to mixed structures derived from two or more of the abovementioned structures. It is also possible to use titanium-containing zeolites having the ITQ-4, SSZ-24, TTM-1, UTD-1, CIT-1 or CIT-5 structure in the process of the present invention. Further titanium-containing zeolites which may be mentioned are those having the ZSM-48 or ZSM-12 structure.

In the process of the present invention, preference is given to using Ti zeolites having the MFI or MEL structure or an MFI/MEL mixed structure. Preference is also given specifically to the Ti-containing zeolite catalysts which are generally referred to as "TS-1", "TS-2", "TS-3", and also Ti zeolites having a framework structure isomorphous with beta-zeolite. In the process of the present invention, very particular preference is given to a zeolite catalyst of the TS-1 type.

Accordingly, the present invention provides a process as described above in which the catalyst used in (v) is a titanium silicalite catalyst of the TS-1 type.

The solvents which can be used in the process of the present invention are subject to essentially no restrictions, as long as it is ensured that the reaction of the alkene used with the above-described hydroperoxides in the presence of the abovementioned catalyst to give the corresponding alkene oxide can be carried out in the presence of this solvent or solvents. Examples of preferred solvents are, inter alia, water,
alcohols, preferably lower alcohols, more preferably alcohols having less than 6 carbon atoms, for example methanol, ethanol, propanols, butanols and pentanols,
diols or polyols, preferably those having less than 6 carbon atoms,
ethers such as diethyl ether, tetrahydrofuran, dioxane, 1,2-diethoxymethane, 2-methoxyethanol,
esters such as methyl acetate or butyrolactone,
amides such as dimethylformamide, dimethylacetamide, N-methylpyrrolidone,
ketones such as acetone,
nitriles such as acetonitrile,
and mixtures of two or more of the abovementioned compounds.

In a preferred embodiment of the process of the present invention, methanol is used as solvent, if desired together with one or more of the abovementioned solvents. Preference is given, inter alia, to water.

Accordingly, the present invention provides a process as described above in which the solvent used in (v) is methanol.

In accordance with the above-described preferred embodiments of the process of the present invention, the present invention thus also provides a process as described above in which the alkene is propene, the hydroperoxide is hydrogen peroxide, the catalyst used is a titanium silicalite catalyst and the solvent is methanol.

The alkene-containing stream S1 provided in (i) can be under any pressure as long as it is ensured that the stream S1 is liquid under the temperature conditions chosen. Furthermore, the pressure range for the compressed stream S1 is dependent on the alkene or alkene mixture used. In the case of propene as is particularly preferably used according to the above description, the propene is present under a pressure in the range from 20 to 35 bar according to a preferred embodiment of the stream S1. The temperature of the stream S1 is preferably in a range from 5 to 30° C., more preferably in a range from 10 to 30° C., particularly preferably in a range from 15 to 30° C. and very particularly preferably in a range from 20 to 30° C.

Accordingly, the present invention also provides a process as described above in which the stream S1 in (i) comprises liquid propene at a pressure in the range from 20 to 35 bar and a temperature in the range from 5 to 30° C.

The stream S1 comprising liquid propene can, in a preferred embodiment, further comprise up to 0.5% by weight, more preferably up to 1% by weight, particularly preferably up to 2% by weight and very particularly preferably up to 4% by weight, of propane.

According to the present invention, at least part of the compressed alkene stream S1 is depressurized in step (ii) with absorption of heat and vaporization of at least part of the liquid alkene. In the process of the present invention, particular preference is given to modes of operation in which the entire stream S1 comprising the alkene or alkenes to be reacted is depressurized and, more preferably, the liquid alkene is totally vaporized on depressurization.

The stream S1 to be depressurized can be depressurized by all suitable methods using all suitable apparatuses. Apparatuses which can be used for the depressurization include, inter alia, valves, stopcocks, diaphragms or throttle valves. The depressurization can be carried out in one or more steps using, for example, the same or at least two different apparatuses for the individual depressurization steps. For the purposes of the present invention, the term "different apparatuses" encompasses apparatuses which are identical except for their dimensions. Different apparatuses in this context are, for example, a valve and a stopcock or two valves of different constructions or two valves of the same construction but of differing sizes.

The pressure under which the gaseous alkene is after depressurization can essentially be chosen at will and is dependent, in particular, on the temperature of the heating medium employed for complete vaporization. In particularly preferred embodiments, the pressure under which the alkene is after depressurization is selected so that a sufficient refrigeration effect is produced at a temperature in the range from −10 to +20° C. by means of the depressurization and vaporization process.

For example, in the case of the particularly preferred propene, pressures of the depressurized propene which are preferably in the range from 4 to 10 bar, more preferably in the range from 5 to 9 bar and particularly preferably in the range from 5 to 8 bar, are chosen.

Accordingly, the present invention also provides a process as described above in which at least part of the stream S1 is depressurized to a pressure in the range from 4 to 10 bar.

In a very particularly preferred embodiment, the pressure to which the alkene is depressurized is selected so that a utilizable refrigeration effect is produced on depressurization of the compressed stream.

The term "utilizable refrigeration effect" as used in the context of the present invention refers to a refrigeration effect which can be used for cooling purposes in at least one process other than the process of the present invention or in the process of the present invention itself or both in at least one process other than the process of the present invention and in the process of the present invention itself.

Cooling can, for example, be carried out in such a way that the heat absorbed during depressurization of the compressed stream S1 is taken from at least one refrigerant. The refrigerant or refrigerants which has/have been cooled in this way can then be used for cooling purposes in the process of the present invention itself or in a process other than the process of the present invention.

Accordingly, the present invention also provides a process as described above in which the refrigeration effect produced in (ii) is transferred to at least one refrigerant.

In addition to all further conceivable refrigerants, preference is given to using, for example, a propylene glycol/water mixture as refrigerant in the process of the present invention.

For the purposes of the present invention, the pressurized alkene stream S1 is preferably depressurized into at least one heat exchanger. In this context, the stream S1 can, for example, be depressurized into a single heat exchanger. It is likewise possible, for example, to depressurize the stream S1 to a particular pressure by introducing it into a first heat exchanger via at least one of the abovementioned depressurization devices, for example a valve, stopcock, diaphragm or throttle valve, and to depressurize the stream S1 which has been depressurized in this first step further by introducing it into at least one further heat exchanger via at least one further depressurization device of the above-mentioned type per heat exchanger. Accordingly, it is possible, for the stream S1 to be firstly partially vaporized in the first heat exchanger and then completely vaporized in the second heat exchanger.

In each of the heat exchangers used, the heat necessary for vaporization can, for example, be taken from at least one refrigerant, where a single refrigerant or a plurality of different refrigerants can be used in each heat exchanger and the refrigerants or refrigerant mixtures used in the individual heat exchangers can be identical or different.

In the process of the present invention, the stream S1 to be depressurized is preferably depressurized into a single heat exchanger using a diaphragm or a valve as depressurization device.

The present invention likewise encompasses embodiments in which the stream S1 is divided into two or more substreams and each of these substreams is depressurized into one heat exchanger. In these likewise preferred embodiments, it is possible, depending on the division of the stream S1, to produce identical or different refrigeration effects in the individual heat exchangers by complete vaporization of the respective substream.

The heat exchanger or exchangers used in the process of the present invention for depressurization of the stream S1 can be of any suitable type. Examples of heat exchanger types are shell-and-tube heat exchangers, coil heat exchangers or plate heat exchangers. In the process of the present invention, preference is given to using a heat exchanger configured as a shell-and-tube heat exchanger.

In a particularly preferred embodiment, the refrigeration effect produced on depressurization of the liquid alkene is used in the process of the present invention itself. This achieves an integrated process. The use of this refrigeration effect can, as described above, be carried out via a refrigerant which is cooled during depressurization of the stream S1 and is then used in at least one further part of the process of the present invention to cool, for example, a feed stream or a product stream in, for example, one or more heat exchangers.

In one particularly preferred embodiment of the process of the present invention, the refrigeration effect produced by depressurization of the stream S1 in the heat exchanger or exchangers is utilized directly. In this context, the term "directly" refers to any mode of operation in which cooling is not effected via a refrigerant.

For the purposes of the present invention, particular preference is in such a case given to embodiments in which heat is taken from one or more streams arising in the process of the present invention in the heat exchanger or exchangers in which the stream S1 is depressurized.

Accordingly, the present invention also provides a process as described above in which the refrigeration effect produced by the depressurization in (ii) is transferred at least partly in at least one heat exchanger to at least one suboperation of the alkene oxide production process.

Possible suboperations of the alkene oxide production process are all process steps in which the refrigeration effect produced in (ii) by depressurization evaporation can be used for a cooling process. Here, it is conceivable, for example, to use the refrigeration effect produced in (ii) in addition to a refrigeration effect provided in another way. Likewise, the refrigeration effect produced in (ii) can be used alone.

In another example of a particularly preferred embodiment of the process of the present invention, the refrigeration effect produced in (ii) is used to provide at least part of the refrigeration effect necessary for the condensation of vapor at the top of one or more distillation columns in the process of the present invention. This is the case especially in the preparation of propylene oxide, preferably in a distillation in which a mixture comprising propylene oxide is worked up and a vapor comprising propylene oxide is obtained.

This is because propylene oxide is a highly reactive compound having a low boiling point, i.e. a boiling point of 35° C. at ambient pressure. Accordingly, the work-up by distillation has to be carried out under mild conditions so that refrigerants have to be used for condensing the vapor at the top of the distillation column.

According to the prior art, such a refrigeration effect is achieved, for example, using refrigeration machines which operate according to compression, vapor jet or absorption principles. Cold vaporization machines operate using closed circulation processes which exploit the heat of vaporization of a liquefied medium for producing the refrigeration effect. The use of such cold vapor machines has the consequence that additional equipment items such as pumps, compressors or vaporizers have to be purchased and operated for providing the refrigeration effect.

The above-described direct use of the enthalpy of vaporization of the alkene used in the process of the present invention, particularly preferably propene, provides, in contrast, a process in which expensive vaporization refrigeration can be obtained at a low temperature level. Of course, as described above, the refrigeration effect can be transferred via at least one refrigerant, although preference is given to the stream S1 to be depressurized being depressurized in a compartment of a heat exchanger, viz. the heating side, while the vapor which is to be cooled and condensed is cooled in another compartment of this heat exchanger, viz. the cooling side.

As described above, the stream S1 to be depressurized in the process of the present invention can, for the purposes of providing the refrigeration effect required for the condensation of the vapor, be divided into two or more substreams, with each of the substreams being depressurized into a heat exchanger and vaporized completely and the vapor being condensed in that heat exchanger in which the required refrigeration effect is made available.

In the work-up by distillation as described above of a mixture comprising an alkene oxide, preferably propylene oxide, in which a vapor comprising essentially alkene oxide, preferably propylene oxide, is obtained, particular preference is given to a mixture consisting essentially of alkene oxide, preferably propylene oxide, together with the solvent used in (v), preferably methanol, and possibly compounds having a boiling point higher than that of the alkene oxide, preferably propylene oxide, being worked up by distillation.

Accordingly, the present invention also provides a process as described above in which the suboperation or suboperations of the alkene oxide production process from which the heat absorbed by the depressurization in (ii) is at least partly taken in at least one heat exchanger is/are the condensation of a vapor.

In particular, the present invention therefore also provides a process as described above in which the suboperation of the alkene oxide production process is the condensation of a vapor which consists essentially of alkene oxide and is obtained in the separation of alkene oxide from a mixture (M1) comprising alkene oxide and at least one solvent by distillation.

In the process of the present invention, it is in principle possible to work-up all mixtures (M1) which comprise alkene oxide and at least one solvent, with the proviso that the vapor as described above results in the work-up by distillation. In particular, it is possible for a mixture obtained in step (v) of the process of the present invention to be worked up by distillation to give the abovementioned vapor.

In a more preferred embodiment of step (v) of the process of the present invention, which will hereinafter be denoted as (v'), a mixture comprising the alkene oxide and the solvent or solvents together with unreacted alkene is obtained. In this case, particular preference is given to subjecting this mixture to at least one further work-up step in which the unreacted alkene is separated off before the mixture is worked up by distillation to give the abovementioned vapor.

In a particularly preferred embodiment of the process of the present invention, the mixture (M1) is obtained by reacting an alkene with a hydroperoxide in the presence of at least one solvent and at least one catalyst to give a mixture comprising the alkene oxide together with unreacted alkene and the solvent or solvents. This mixture will hereinafter be referred to as (M0). Before the distillation from which the vapor consisting essentially of alkene oxide results, the unreacted alkene is separated off from this mixture (M0) in at least one upstream step and the mixture (M1) is obtained from this alkene removal.

Accordingly, the present invention also provides a process as described above in which the mixture (M1) is obtained from a process which comprises the steps (v') and (vi):

(v') reacting the alkene obtained in (ii) with a hydroperoxide in the presence of at least one solvent and at least one catalyst to give a mixture M(0) comprising alkene oxide, unreacted alkene and the solvent or solvents;

(vi) separating the unreacted alkene from the mixture (M0) to give a mixture (M1) comprising alkene oxide and the solvent or solvents.

The reaction of the alkene, preferably propene, in (v') with the hydroperoxide, preferably hydrogen peroxide, in the presence of the solvent or solvents, preferably methanol, and the catalyst or catalysts, preferably the above-described titanium silicalite catalyst, can be carried out in one, two or more stages, particularly preferably in two stages.

Based on the abovementioned preferred compounds, a two-stage reaction takes place, for example, as follows:

(a) the hydrogen peroxide is reacted with propene to give a mixture comprising propylene oxide and unreacted hydrogen peroxide;

(b) the unreacted hydrogen peroxide is separated off from the mixture resulting from stage (a);

(c) reacting the hydrogen peroxide which has been separated off in stage (b) with propene.

Accordingly, the reaction of propene with hydrogen peroxide takes place, as indicated, in two stages (a) and (c) between which there is a separation stage (b).

The isolation of the hydrogen peroxide in the separation stage (b) can, for the purposes of the present invention, be carried out using all customary separation methods of the prior art.

The hydrogen peroxide is preferably separated off by distillation. Depending on the requirements of the process, it can be separated off in one or more distillation columns. Preference is given to using one distillation column in a separation stage.

The reaction of propene with hydrogen peroxide in the process of the present invention takes place in a reactor suitable for this purpose. Starting materials used for the reaction are propene, hydrogen peroxide and methanol. In the process, the starting materials can be introduced individually into the reactor or preferably be combined to form a single stream before being fed into the reactor. In the process of the present invention, preference is given to introducing one stream which consists of a combination of the starting materials into the reactor. Here, preference is given to a stream in which the concentrations of the individual starting materials forming the stream are selected so that the stream is liquid and consists of a single phase.

In a further, preferred embodiment, it is possible to carry out the reaction in stages (a) and (c) in two separate reactors.

As reactors, it is of course possible to use all conceivable reactors which are best-suited to the respective reaction. Here, the term "a reactor" is not restricted to a single vessel. Rather, it is also possible to use a cascade of stirred vessels as reactor.

Preference is given to using fixed-bed reactors as reactors. The fixed-bed reactors used are more preferably fixed-bed tube reactors.

In the case of reactions in two separate reactors in stages (a) and (c), particular preference is given to using one isothermal fixed-bed tube reactor and one adiabatic fixed-bed reactor. Preference is given to using the isothermal fixed-bed tube reactor in stage (a) and the adiabatic fixed-bed reactor in stage (b).

After the reaction of the alkene, preferably propene, with hydroperoxide, preferably hydrogen peroxide, to give a mixture (M0) comprising alkene oxide, preferably propylene oxide, unreacted alkene, preferably propene, and solvent, preferably methanol, particular preference is given to separating off unreacted alkene, preferably propene, from this mixture (M0).

The unreacted alkene is preferably separated off from (M0) by distillation. It is in principle possible to use any number of columns for this purpose. Preference is given to using one column. This column generally has at least 5, preferably at least 10 and more preferably at least 15, theoretical plates. The distillation in this column is preferably carried out at pressures in the range from 0.5 to 25 bar, more preferably from 0.7 to 5 bar and particularly preferably in the range from 0.9 to 1.5 bar.

The removal of the unreacted propene carried out in the preferred case sometimes suffers from the problem that during the removal of the propene as a low-boiling fraction, oxygen can accumulate in this low-boiling fraction in a concentration which makes the low-boiling fraction an ignitable mixture. This can give rise to a serious safety risk when propene is in turn separated off from the low-boiling fraction by distillation, which is preferred when the propene is, as preferred in one embodiment of the process of the present invention, to be returned to the process as starting material.

This problem can be solved, for example, by the propene being removed from the low-boiling mixture by distillation and an inert solid having a boiling point lower than that of propene, preferably nitrogen or for example methane, being added in the upper part of the separation apparatus used for this purpose in such an amount that the oxygen is diluted to a concentration at which the mixture is no longer ignitable. This method is described, for example, in EP-B 0 719 768. However, the problem is preferably solved by using a process for the work-up of a mixture comprising propene and oxygen in which oxygen is removed from the mixture by means other than distillation to give a further mixture and separating the propene from the further mixture by distillation. This method is described in DE-A 100 01 401.1, whose relevant contents are fully incorporated by reference into the disclosure of the present patent application.

In this process, the oxygen is separated from a mixture (M1) comprising alkene and oxygen, preferably by, e.g., combustion or by reaction of the oxygen with a suitable chemical compound. The combustion is preferably carried out in the presence of a suitable catalyst, such as a supported noble metal catalyst, wherein temperatures of from 280 to 580° C. are preferably employed. As suitable chemical compound used for the separation of the oxygen, among others, an alkene is preferably to be mentioned, said alkene being preferably comprised already in (M1). As preferred reaction of the alkene, such as propane, with the oxygen, an oxydehydrogenation is to be mentioned, which is further preferably carried out in the presence of a suitable catalyst. Suitable catalysts are, e.g., described in M. Xu, React. Kinet. Catal. Lett. 57 (1996), pages 3 to 11, or in B. Delmon, Stud. Surf. Sci. Catal. 110 (1997), pages 43 to 59.

In a preferred embodiment of the process of the present invention, the mixture (M1) comprises propylene oxide in a proportion of from 5 to 15% by weight, preferably from 6 to 12% by weight and particularly preferably from 8 to 10.5% by weight, and methanol in a proportion of from 55 to 85% by weight, preferably from 60 to 80% by weight and particularly preferably from 65 to 75% by weight.

In a further, preferred embodiment of the process of the present invention, the above-described vapor stream consisting essentially of alkene oxide is compressed and subsequently condensed. The heat evolved in this condensation can, in a preferred embodiment, be at least partly recirculated into the process of the present invention, preferably into at least one vaporizer of a distillation column and more preferably into at least one vaporizer of the distillation column in which the mixture (M1) is distilled to give a vapor stream consisting essentially of alkene oxide. In a more preferred embodiment of the process of the present invention, part of the condensate obtained is subsequently cooled further and introduced as runback into the distillation column from which the vapor stream mentioned is obtained. This step comprising further cooling of the condensate preferably takes place in a heat exchanger in which the condensate is preferably cooled to from 10 to 30° C., particularly preferably from 12 to 20° C. The refrigeration effect necessary for this purpose is, for example, particularly preferably obtained by depressurizing the compressed alkene stream on the heating side of this heat exchanger so that it is at least partially, preferably completely, vaporized, as is described above in the context of the present invention.

Accordingly, the present invention also provides a process as described above in which, in at least one of the heat exchangers used in (ii), the heat is at least partly taken from a vapor condensate obtained in step (cc) of a process comprising at least the steps (aa) to (dd):

(aa) separating alkene oxide by distillation from a mixture (M1) comprising alkene oxide and at least one solvent using a distillation column to give a bottom stream and a vapor stream consisting essentially of alkene oxide;
(bb) compressing the vapor stream obtained in (aa) by means of at least one compressor to give a compressed vapor;
(cc) condensing the vapor obtained in (bb) and recirculating at least part of the heat of condensation into at least one vaporizer used in the distillation column employed in (aa);
(dd) cooling at least part of the condensate obtained in (cc) in at least one heat exchanger to a temperature in the range from 12 to 20° C. and returning at least part of the cooled condensate as runback to the distillation column used in (aa).

In (dd), preference is given to not introducing all the condensate obtained from (cc) into the heat exchanger or heat exchangers. More preferably, the part which is cooled in the heat exchanger or heat exchangers is returned in its entirety as runback to the distillation column used in (aa).

The heat exchanger used in (dd) can be of essentially any type. Examples of types of heat exchangers are shell-and-tube heat exchangers, coil heat exchangers and plate heat exchangers. For the purposes of the present invention, preference is given to using a heat exchanger configured as a shell-and-tube heat exchanger.

According to the present invention, the depressurized and vaporized alkene stream obtained from (ii) is used as starting material for the reaction in (v). This alkene stream can, for example, be introduced as such into the apparatus or apparatuses used for the reaction, for example the reactors described above for the steps (a) and (c).

In the process of the present invention, preference is given to dissolving the depressurized and vaporized, gaseous alkene stream in at least one of the solvents used before it is introduced into the apparatus used for the reaction. In the case of the preferred propene, the vaporized, depressurized propene stream is accordingly dissolved in methanol before being introduced into the apparatus or apparatuses used for the epoxidation.

Accordingly, the present invention also provides a process as described above which further comprises the steps (iii) and (iv):
(iii) dissolving the gaseous alkene obtained in (ii) in at least one of the solvents used in (v) or (v') to give a solution;
(iv) introducing the solution obtained in (iii) into the apparatus used for the reaction of (v) or (v').

The dissolution in (iii) can in principle be carried out using all suitable methods and modes of operation. Preference is given to drawing the alkene into an ejector and dissolving it in the solvent, with the ejector very particularly preferably being operated using this solvent as driving fluid. In the above-described preferred embodiment, the gaseous propene obtained from (ii) is, in (iii), dissolved in methanol using an ejector operated using methanol as driving fluid and the solution obtained is, in (iv), introduced into the apparatus used for the reaction of (v) or (v').

If, as described above, the stream S1 is divided into two or more substreams and each of the substreams is depressurized into one heat exchanger and completely vaporized, the gaseous substreams obtained are, in a preferred embodiment of the process of the present invention, combined after leaving the heat exchangers and dissolved together in an ejector.

The heat of solution evolved on dissolution of the alkene oxide in the solvent can, for example, be utilized in the process of the present invention or in another process. This heat of solution is particularly preferably removed via a heat exchanger by means of conventional river water. This removal of the heat of solution preferably occurs at from 25 to 45° C.

Accordingly, the present invention also provides a process as described above in which the heat of solution evolved in (iii) is removed by means of river water.

This specific way of operating the process of the present invention makes it possible for a refrigeration effect which could otherwise be made available only by means of expensive measures to be obtained at a low temperature level, for example in the range from 3 to 10° C., by means of the depressurization vaporization of the alkene stream and, in addition, to remove the enthalpy of solution of the alkene evolved in (iii) in an inexpensive manner by means of river water.

The solvent used for operating the ejector, particularly preferably methanol, is preferably circulated in the process of the present invention. The solvent in which the depressurized alkene is dissolved is accordingly, in a preferred embodiment, separated off from the mixture (M1), with the work-up by distillation of the mixture (M1) preferably being carried out so that the vapor stream consisting essentially of alkene oxide contains an amount of solvent which does not exceed 500 ppm, preferably 200 ppm, more preferably 100 ppm, more preferably 50 ppm, more preferably 20 ppm, particularly preferably 15 ppm and very particularly preferably 10 ppm, in each case based on the total weight of the alkene oxide fraction separated off.

The separation of the solvent, preferably methanol, from (M1) is preferably carried out by distillation. In a particularly preferred process in which propene in methanol is reacted with an aqueous hydrogen peroxide solution, the separation by distillation gives, for example, a bottom stream comprising methanol and water. In a further, preferred embodiment, water is separated off from this bottom stream comprising methanol and water and a stream comprising methanol and water resulting from this separation is recirculated to the process. This latter recirculated stream contains at least 3% by weight, preferably from 3 to 10% by weight, of water, based on the total weight of the stream. In the above-described reaction of propene, the bottom stream more preferably comprises not only methanol and water but also methyl formate. This process therefore preferably comprises the following steps:

separating water from the bottom stream to give a stream A1 comprising methanol, methyl formate and water;

separating methyl formate from the stream A1 to give a stream A2 comprising methanol and water;

recirculating the stream A2 to the process, with A2 containing an amount of water which is within the above-mentioned limits.

Especially preferably, A2 is recirculated as solvent to (a) and/or (c), preferably (a), wherein, e.g., the alkene may be at least partially dissolved in A2 according to the present invention.

The present invention therefore also provides a process as described above in which the solvent used in (iii) is circulated.

The present invention is illustrated by the following example.

EXAMPLE

Using a method corresponding to the process described in WO 00/07965, propylene oxide is prepared from propene by reaction with hydrogen peroxide in methanol as solvent using a TS-1 catalyst.

A refrigeration effect of 84 kWh/t (propene) at a temperature of 3.5° C. was obtained by depressurization and complete vaporization of 1 metric ton of liquid propene from 30 bar and 25° C. to a pressure of 6.3 bar. The subsequent dissolution of the gaseous propene in methanol was carried out by means of an ejector as supplied, for example, by GEA Jet Pumps. To dissolve 1 metric ton of propene, 7 metric tons of methanol, which was employed as solvent in the reaction, were used as driving fluid.

The propene-containing methanol from which the heat of solution had been removed at 35° C. by means of river water was then fed into an appropriate oxidation reactor for the reaction of propene with hydrogen peroxide.

Part of the refrigeration effect of 84 kWh/t (propene) obtained was used in the propylene oxide production process for condensing the vapor from the propylene oxide distillation, with the propylene oxide being separated from the residual solvent.

We claim:

1. A process for preparing an alkene oxide, comprising
   (i) providing a stream S1 comprising a compressed, liquid alkene;
   (ii) depressurizing at least part of the stream S1 with absorption of heat and with at least partial vaporization of the liquid alkene; and
   (iii) reacting the alkene obtained in (ii) with a hydroperoxide in the presence of at least one solvent and at least one catalyst to form a mixture comprising an alkene oxide and the at least one solvent.

2. A process as claimed in claim 1, wherein the alkene is propene, the hydroperoxide is hydrogen peroxide, the catalyst is a titanium silicalite catalyst and the solvent is methanol.

3. A process as claimed in claim 2, wherein the stream S1 in (i) comprises liquid propene at a pressure in the range from 20 to 35 bar and a temperature in the range from 5 to 30° C.

4. A process as claimed in claim 2, wherein at least part of the stream S1 is depressurized to a pressure in the range from 4 to 10 bar.

5. A process as claimed in claim 1, wherein in (ii) the stream S1 is depressurized into at least one heat exchanger and the heat absorbed during depressurization is taken from at least one refrigerant to form a cooled refrigerant, and wherein the cooled refrigerant is used for cooling purposes in at least one sub-operation of the process.

6. A process as claimed in claim 5, wherein the sub-operation of the process includes condensing a vapor which consists essentially of the alkene oxide and is obtained by separating the alkene oxide from a mixture (M1) comprising the alkene oxide and the at least one solvent by distillation.

7. A process as claimed in claim 6, wherein the mixture (M1) is obtained from a process comprising:
   (iv) reacting the alkene obtained in (ii) with a hydroperoxide in the presence of at least one solvent and at least one catalyst to give a mixture (M0) comprising the alkene oxide, the alkene and the at least one solvent; and
   (v) separating the alkene from the mixture (M0) to give a mixture (M1) comprising the alkene oxide and the at least one solvent.

8. A process as claimed in claim 7, which further comprises:
   (vi) dissolving the vaporized alkene obtained in (ii) in at least one of the solvents used in (iii) or (iv) to give a solution;
   (vii) introducing the solution obtained in (vi) into the apparatus used for the reaction of (iii) or (iv).

9. A process as claimed in claim 8, wherein on dissolution of the alkene oxide in (vi) heat of solution is evolved, and said heat of solution is removed via a heat exchanger by means of river water.

10. A process as claimed in claim 8, wherein the solvent used in (iii) is circulated.

11. A process for preparing an alkene oxide, which comprises:
   (i) providing a stream S1 comprising a compressed, liquid alkene;
   (ii) depressurizing at least part of the stream S1 with absorption of heat and with at least partial vaporization of the liquid alkene; and
   (iii) reacting the alkene obtained in (ii) with a hydroperoxide in the presence of at least one solvent and at least one catalyst to form a mixture comprising an alkene oxide and the at least one solvent,
      wherein the alkene is propene, the hydroperoxide is hydrogen peroxide, the catalyst is a titanium silicalite catalyst and the solvent is methanol.

12. A process as claimed in claim 11, wherein in (ii) the stream S1 is depressurized into at least one heat exchanger and the heat absorbed during depressurization is taken from at least one refrigerant to form a cooled refrigerant, and wherein the cooled refrigerant is used for cooling purposes in at least one sub-operation of the process.

13. A process as claimed in claim 12, wherein the sub-operation of the process includes condensing a vapor which consists essentially of the alkene oxide and is obtained by separating the alkene oxide from a mixture (M1) comprising the alkene oxide and at least one solvent by distillation.

14. A process as claimed in claim 13, wherein the mixture (M1) is obtained from a process comprising:
   (iv) reacting the alkene obtained in (ii) with a hydroperoxide in the presence of at least one solvent and at least one catalyst to form a mixture (M0) comprising the alkene oxide, the alkene and the at least one solvent; and
   (v) separating the alkene from the mixture (M0) to form a mixture (M1) comprising the alkene oxide and the at least one solvent.

15. A process as claimed in claim 14, which further comprises:
   (vi) dissolving the alkene obtained in (ii) in at least one of the solvents present in the reacting (iii) or the reacting (iv) to form a solution;
   (vii) introducing the solution obtained in (vi) into an apparatus in which the reacting (iii) and (iv) is carried out.

16. A process for preparing an alkene oxide, which comprises:
   (i) providing a stream S1 comprising a compressed, liquid alkene;
   (ii) depressurizing at least part of the stream S1 with absorption of heat and with at least partial vaporization of the liquid alkene;
   (iii) reacting the alkene obtained in (ii) with a hydroperoxide in the presence of at least one solvent and at least one catalyst to form a mixture comprising the alkene oxide and the at least one solvent;
      wherein the alkene is propene, the hydroperoxide is hydrogen peroxide, the catalyst is a titanium silicalite catalyst and the solvent is methanol,
      wherein in (ii) the stream S1 is depressurized into at least one heat exchanger and the heat absorbed by the alkene during the depressurizing is taken from at least one refrigerant to form a cooled refrigerant, and wherein the cooled refrigerant is used for cooling purposes in at least one sub-operation of the process,
      wherein the sub-operation of the process includes condensing a vapor which consists essentially of the alkene oxide and is obtained by separating the alkene oxide from a mixture (M1) comprising the alkene oxide and the at least one solvent by distillation, and wherein the mixture (M1) is obtained from a process comprising:
   (iv) reacting the alkene obtained in (ii) with a hydroperoxide in the presence of at least one solvent and at least one catalyst to give a mixture (M0) comprising the alkene oxide, the alkene and the at least one solvent; and
   (v) separating the alkene from the mixture (M0) to form a mixture (M1) comprising the alkene oxide at the at least one solvent; and
   wherein the process further comprises:
   (vi) dissolving the alkene obtained in (ii) in at least one of the solvents present during the reacting (iv) or the reacting (iii) to form a solution; and
   (vii) introducing the solution obtained in (vi) into an apparatus in which the reacting (iii) or the reacting (iv) is carried out.

* * * * *